(12) United States Patent
Müller-Hartmann et al.

(10) Patent No.: US 8,101,401 B2
(45) Date of Patent: Jan. 24, 2012

(54) CONTAINER AND DEVICE FOR GENERATING ELECTRIC FIELDS IN DIFFERENT CHAMBERS

(75) Inventors: Herbert Müller-Hartmann, Köln (DE); Michael Habig, Basel (CH)

(73) Assignee: Lonza Cologne GmbH, Cologne (DE)

( * ) Notice: Subject to any disclaimer, the term of this patent is extended or adjusted under 35 U.S.C. 154(b) by 1222 days.

(21) Appl. No.: 11/079,192

(22) Filed: Mar. 15, 2005

(65) Prior Publication Data

US 2006/0087522 A1    Apr. 27, 2006

(30) Foreign Application Priority Data

Mar. 15, 2004   (EP) .................................... 04006058

(51) Int. Cl.
*C12M 1/42* (2006.01)
*C12M 3/00* (2006.01)
*C12N 13/00* (2006.01)

(52) U.S. Cl. ............... 435/285.2; 435/173.1; 435/173.4; 435/173.5; 435/173.6; 435/288.3; 435/288.4

(58) Field of Classification Search ............... 435/285.2, 435/173.1, 173.4, 173.5, 173.6, 288.3, 288.4
See application file for complete search history.

(56) References Cited

U.S. PATENT DOCUMENTS

| | | | |
|---|---|---|---|
| 4,072,578 A * | 2/1978 | Cady et al. ................. | 435/287.1 |
| 4,765,874 A * | 8/1988 | Modes et al. ................. | 205/635 |
| 4,882,281 A | 11/1989 | Hilliard et al. | |
| 5,183,744 A | 2/1993 | Kawamura et al. | |
| 5,563,067 A * | 10/1996 | Sugihara et al. ........... | 435/287.1 |
| 2002/0028480 A1 | 3/2002 | Maher et al. | |
| 2004/0180426 A1* | 9/2004 | Maher et al. ................ | 435/287.2 |
| 2005/0070018 A1 | 3/2005 | Johnson et al. | |
| 2005/0112544 A1* | 5/2005 | Xu et al. ........................... | 435/4 |
| 2006/0115888 A1* | 6/2006 | Gamelin et al. ........... | 435/285.2 |

FOREIGN PATENT DOCUMENTS

| | | |
|---|---|---|
| DE | 199 17 571 A1 | 11/2000 |
| DE | 100 33 578 A1 | 1/2002 |
| GB | 2 386 949 A | 10/2003 |
| WO | WO 03/049806 A1 | 6/2003 |
| WO | WO 03/057819 A1 | 7/2003 |
| WO | WO 2004/050866 A1 | 6/2004 |
| WO | WO 2005/042696 A2 | 5/2005 |
| WO | WO 2005/044983 A2 | 5/2005 |

* cited by examiner

*Primary Examiner* — Nathan Bowers (74) *Attorney, Agent, or Firm* — Joyce von Natzmer; Pequinot + Myers, LLC

(57) ABSTRACT

The invention concerns a container 1 with chambers 2 which each comprise at least one pair of electrodes including a first 4 and a second electrode 5 for the application of electric voltage for generating an electric field within one chamber 2. At least two first electrodes 4 of different chambers 3 are conductively coupled and at least one second electrode 5 of said chamber 2 is separately conductively connectable. The invention further concerns a method for manufacturing said container 1 as well as a device for electrically contacting at least one of said containers 1.

22 Claims, 7 Drawing Sheets

CONTAINER AND DEVICE FOR GENERATING ELECTRIC FIELDS IN DIFFERENT CHAMBERS

This application claims priority to European application No. 04006058.4, filed Mar. 15, 2004, which is incorporated herein by reference in its entirety.

FIELD OF THE INVENTION

The invention concerns a container with chambers which each comprise at least one pair of electrodes including a first and a second electrode for the application of electric voltage for generating an electric field within one chamber. The invention further concerns a method for manufacturing said container as well as a device for electrically contacting at least one of said containers.

BACKGROUND OF THE INVENTION

Containers with several chambers of the nature mentioned above are well-established and are mainly used in biochemical and pharmaceutical applications if a plurality of probes has to be tested simultaneously. Special applications are, for example, electroporation, electrofusion and electrostimulation of living cells as well as all applications with which the probe has to be exposed to an electric field. The aim is to provide a large number of chambers, e.g. 96 or 384, especially with HT-analyses (HT=high throughput), as a maximum amount of samples is to be tested in a minimum time frame. Usually such containers are called multiwell plates, microtiter plates or multiwells.

Usually the known containers consist of several chambers that are provided with two electrodes, respectively, which are in contact with the probe, e.g. a cell suspension in the chamber. The two electrodes of a chamber generate an electric field within the chamber if an electric voltage is applied, whereby they show different polarities, for example, when direct current is used. The electrodes of same polarity of different chambers, i.e. all cathodes and/or all anodes, are all made of one piece or are coupled electrically so that they can be electrically connected via a common voltage source. Such arrangements have the advantage of a relatively simple assembly but, however, it is a disadvantage that the electrical parameter for all chambers is the same and consequently the individual operation of individual chambers is not possible.

Devices for the electrical stimulation of living cells are well-known, for example from US 2002/0028480 A1. In one embodiment, band-like electrodes are arranged in pairs on the ground of a multiwell plate. The band-like electrodes respectively protrude into the individual chambers of said plates and thus are in electric contact with the probes. Each band-like electrode has a contact area at one of its open ends, to which a voltage generator can be connected. One pair of electrodes is respectively assigned to one row of chambers. In a special embodiment some of the electrodes, e.g. all anodes, are short-circuited while the respective other part of electrodes of a row, e.g. the cathodes, are connected separately. In each case, however, with these well-known arrangements only entire rows of chambers can be activated, i.e. electrical parameter can only be adjusted for entire groups of chambers and not individually for each chamber.

From DE 199 17 571 A1 an electrode array for electroporation assays is known that consists of a planar arrangement of electric conducting paths on the surface of an electric insulator. The conducting paths are arranged in oppositely arranged ramifications and comprise single reaction areas for receiving probes for electroporation. The oppositely arranged conducting paths act as electrodes when an electric voltage is applied, whereby the respective conducting paths merge in a single main path that is connected to the voltage generator. As a consequence, even with this known arrangement no variable adjustment of electric parameter is possible so that all reaction areas are exposed to the same electric conditions.

WO 03/057819 A1 describes, among other things, also multiwell plates where the electrodes of different chambers are electrically connected at least in pairs so that the electrical parameter can be adjusted only for single groups of chambers and not for each chamber individually.

There is a need for a container as mentioned above that enables a flexible, individual and fast generation of electric fields in individual chambers of a container as well as a device for the safe and reliable electrical contacting of said container. Furthermore, there is a need for an inexpensive manufacturing method for such a container.

BRIEF SUMMARY OF THE INVENTION

According to the invention this need is addressed by a container of the kind mentioned above, wherein at least two first electrodes of different chambers are conductively coupled and at least one second electrode of said chamber is separately conductively connectable. Thus, each chamber of a container can be separately selected, controlled and switched, respectively, in an easy manner so that the probes can be exposed to different conditions. With this container according to the invention a lot of samples can be tested under different conditions within a short time, without having to change the container or the probes, so that the container according to the invention is especially suited for automated HT-methods. As some electrodes are conductively connected the technical complexity as far as the contacting of electrodes is concerned can be minimized.

At least a group of electrodes of the same polarity or all electrodes of the same polarity, i.e. those that have the same polarity if direct current is applied and that are allocated to different chambers, can be conductively coupled so that on the one hand the method according to the invention can be accelerated and on the other hand contacting of the electrodes can be simplified.

In an advantageous embodiment of the invention specific contact areas that are electrically contactable for the application of said electric voltage are allocated to said electrodes. The at least two coupled electrodes of different chambers are contactable by means of a common contact area. Consequently, manufacturing can be simplified and the amount of necessary electric contacts and wires, respectively, can be minimized.

In a special embodiment of the container according to the invention it is provided that the respective second electrode of a chamber has a contact area that is specifically allocated to it. This embodiment of the container ensures that the respective electrodes can be contacted directly and safely for the separate activation of a single container. Thus, in a preferred embodiment of the invention it is provided that said contact areas are directly attached to the electrodes.

In an advantageous embodiment of the invention the electrodes are disposed at the bottom side of (underneath) the electrodes on the ground of the container so that they can be contacted from the bottom and the container stays accessible from the top and the sides which is an advantage especially with automatic methods. The contact area can take the lower bottom of the electrode at least entirely which has a positive effect on the homogeneous distribution of the electric field within the chamber if the electrodes consist of conductive polymers.

For specific applications, especially for HT-applications, it is suggested that a plurality of chambers, preferably 6, 8, 12, 16, 24, 32, 48, 64, 96, 128, 192, 384, 1536, 3456 or 6144, are provided.

In an advantageous embodiment of the invention several chambers are disposed in a row or at least two parallel rows and at least a part of the electrodes which are disposed on the same side of the different chambers of one row is conductively coupled. By this special arrangement manufacture of the container is considerably simplified and furthermore it is less expensive as material costs can be reduced.

As at least two oppositely arranged electrodes of different chambers of adjacent rows are coupled conductively, manufacture of the container according to the invention can be simplified and executed in a less expensive manner.

At least one electrode can consist of e.g. a metal, preferably gold, silver or aluminium.

In a particularly advantageous embodiment of the invention it is provided that at least one electrode consists of a polymer that is doped with a conductive material, in particular fibres of carbon, graphite, carbon black and/or carbon-nanotubes, preferably in a concentration of 40 to 80% w/w. The polymer can be, for example, polycarbonate, polyetheretherketone, polypropylene, polyamide, preferably polyamide 6 or polyamide 66, polyphenylensulfide or a mixture of these polymers or contain one or several of these polymers as main component. Such polymer electrodes with high conductivity can be produced in an injection-moulding process and they do not release cytotoxic substances that could influence or impair the test results.

In an advantageous embodiment of the invention said contact area comprises a contact material which is attached to said electrode and has a lower specific resistance or boundary resistance at a temperature of 23° C. than the material of which said electrode consists. Preferably said contact material is a metal, preferably copper, or an intrinsically conductive synthetic material and/or said contact material has a specific resistance at a temperature of 23° C. below $1\times10^{-5}$ Ohm·cm, preferably of $1\times10^{-6}$ to $2\times10^{-6}$ Ohm·cm. Especially with the Use of polymer electrodes that have a relatively high input resistance the overall resistance of the electrodes can be reduced considerably by effect of the contact material.

The problem is also solved by a method for manufacturing a container, wherein at first a wall area that builds the chambers and comprises at least two spared areas per chamber is injection-moulded of a non-conductible polymer and subsequently the spared areas are provided with a conductible material, or wherein firstly at least two areas per chamber are produced of a conductive material or placed in a moulding frame and subsequently a wall area that builds the chambers is injection-moulded of a non-conductible polymer around said at least two areas, wherein at least two areas of different chambers, which include conductive material, are conductively coupled to each other and at least the respective other area of a chamber is provided with a separate connection to the electric contact. This method enables the trouble-free and inexpensive production of containers according to the invention.

In a particularly advantageous embodiment of the method of manufacture it is provided that for electrically contacting a contact material is attached to the conductive material, or a contact material, preferably a metal or an intrinsically conductive synthetic material, is attached to the conductive material by effect of pressure and/or heat, preferably by hot embossing and/or by effect of an adherent layer that preferably has a lower specific resistance.

With this manufacturing method preferably at least a group of chambers or all chambers are connected conductively via at least one respective area with conductive material.

The conductive material may be, for example, metal electrodes, preferably of gold, silver or aluminium, which can be put into the spared areas. Alternatively, one can injection-mould around said conductive material after it was placed in a moulding frame.

In an alternative and more preferred manufacturing method as a conductive material polymer electrodes, preferably of a polymer that is doped with a conductive material, especially carbon fibres, graphite, soot and/or carbon-nanotubes, preferably in an concentration of 40 to 80% w/w, may be injection-moulded in a moulding frame or in said spared areas.

Furthermore, the problem is solved by a device for electrically contacting as mentioned above, wherein one contact element, respectively, is provided for at least one second electrode, respectively, of one chamber of said container, and some contact elements, preferably 1 to 6, are provided for said electrically coupled first electrodes. In this embodiment, the second electrodes that are not coupled are respectively contacted by one contact element so that the respective chamber can be switched separately. As only some contact elements are necessary for the coupled first electrodes, constructional efforts can be reduced and thus the production of the device according to the invention can be simplified. The contact elements may be pin contacts, spring contacts or the like.

In an advantageous embodiment of the invention a construction, preferably a plate, is provided on which said contact elements are arranged, whereby the construction is mobile vertically and/or horizontally, in particular by means of a motor.

Preferably a platform for the installation of said container is provided, which is mobile horizontally and/or vertically, especially by means of a motor. The platform has at least one opening or is a punched plate, whereby the number of holes preferably corresponds to the number of contact elements. The openings or holes serve for inserting the contact elements in order to contact the electrodes.

Furthermore, an inner space is provided in which said contact elements are disposed, and/or at least one opening is provided through which said contact elements can be inserted. Thus, the electric contacts are arranged in the inner space of the device so that the security of the persons who operate the device is granted.

It is an advantage of this embodiment that an opening of a housing is provided through which the container and/or the platform can be inserted into the inner space, which increases the security of the device.

In an advantageous embodiment, the device according to the invention can comprise at least one storage unit or being connectable to at least one storage unit, whereby said storage unit preferably is a capacitor. It is also possible that several storage units are connected parallel or serial.

Furthermore, at least one switch element is disposed between said storage unit and said electrodes of said container, and/or wherein a switch element is allocated to each inner space and/or each group of coupled electrodes, whereby the switch element preferably is a relay. By operating (controlling) the switch elements individual electrodes or chambers can be switched specifically and safely.

In a special embodiment of the invention it is provided that the switch elements are directly attached to the contact elements, preferably underneath the construction on which the contact elements are arranged. This advantageous arrangement enables a very compact construction of the device according to the invention.

The invention is described below in detail with reference to the drawings.

VARIOUS AND PREFERRED EMBODIMENTS OF THE INVENTION

Figure 1:
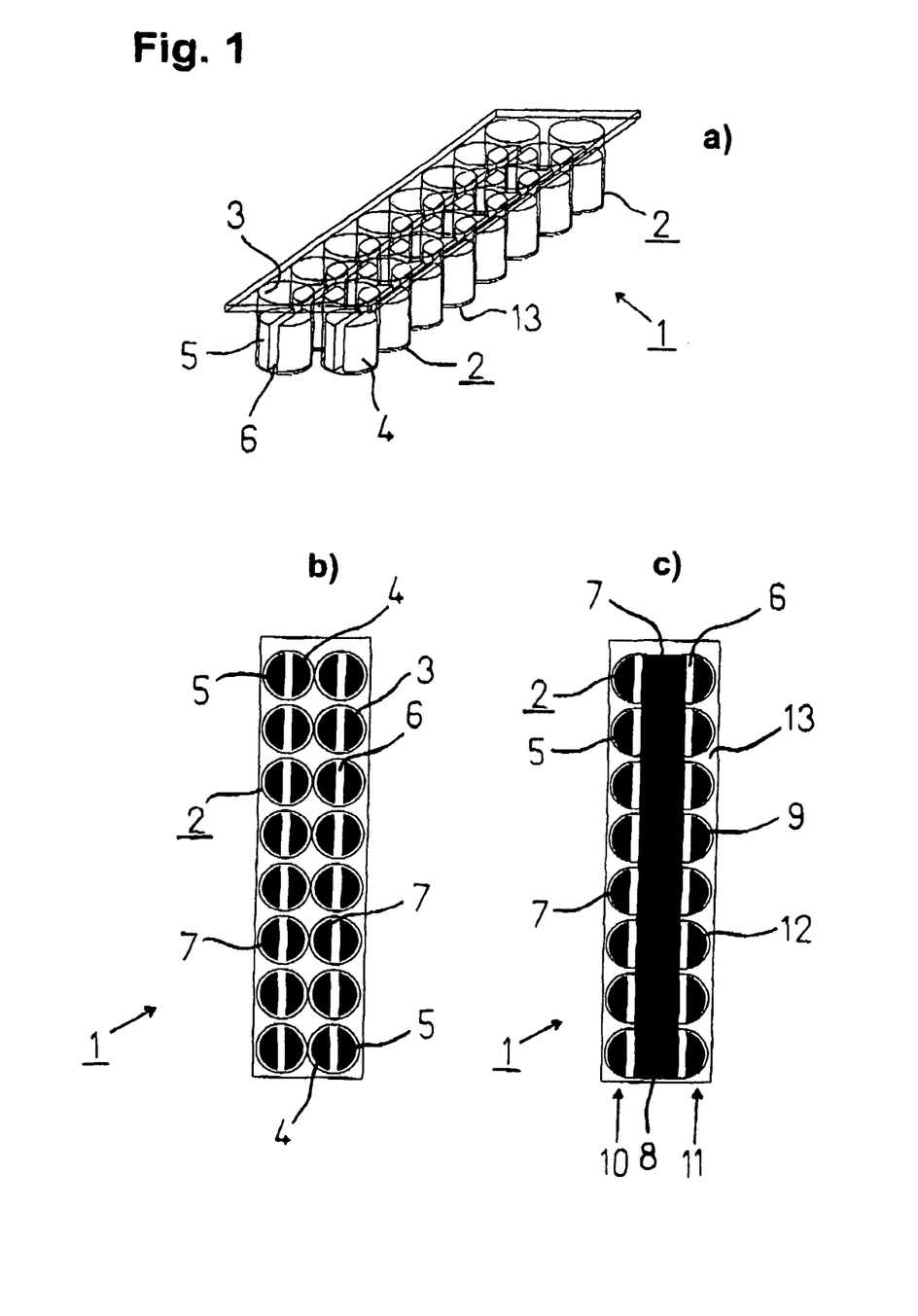
FIG. 1 schematically shows different views of an embodiment of the device according to the invention for demonstration of the method according to the invention
 a) perspective view
 b) top view
 c) bottom view

FIG. 1 shows different views of a particularly advantageous embodiment of a container 1 according to the invention. The container 1 is depicted in a) perspective view, b) top view, and c) bottom view. The container 1 according to the invention comprises 16 chambers 2 which each are built by a wall area 3. Each chamber 2 comprises a pair of electrodes which includes a first electrode 4 and a second electrode 5. While the wall area 3 consists of a non-conductive material, for example glass or plastics, the electrodes 4, 5 are made of an electroconductive material. For example, the electrodes 4, 5 may thereby consist of a metal, i.e. aluminium, copper, silver or gold. However, electrodes made of a polymer which is doped with a conductive material are preferred. In this case, the dope may comprise, for example, fibres of carbon, graphite, carbon black (soot) and/or carbon nanotubes. Said Polymer may comprise a concentration of 40-80% w/w of dope. Such conductive polymers are beneficial because they can be easily produced in an injection moulding process at favourable costs and, contrary to electrodes made of metal, do not release cytotoxic metal ions. The concentration of the dope within the polymer should be chosen such that on the one hand the polymer has a sufficient conductivity and on the other hand injection-moulding is still possible. These features are ensured within a range of concentration of 40-80% w/w.

In each chamber 2, the first electrode 4 and the second electrode 5 define a gap 6 that serves for receiving a suspension of cells in which biologically active molecules, e.g. nucleic acids, are solved in addition to living cells. When voltage is applied to the pair of electrodes an electric current flows through the suspension of cells in the gap 6, which causes transfer of said biologically active molecules into said living cells. This technique is commonly known as electroporation. Both electrodes 4, 5 have opposite polarities when voltage is applied, i.e. one electrode 4, 5 shows a negative potential and thus serves as a cathode while the other electrode 4, 5 shows a positive potential and hence acts as anode. Thus, depending on the direction of current flow the first electrode 4 and the second electrode 5, respectively, may act as cathode or anode, wherein the perspective polarity is not important in respect of the present invention. For example, using direct current the opposite polarities are fixed while using alternating current the polarities resonate bidirectionally so that an alternating field is generated.

Contact areas 7 are allocated to each electrode 4, 5 for establishing the electric contact. Said contact areas 7 may be, for example, connected to a storage unit, preferably a capacitor, which can be selectively discharged for generating the electric field in the gap 6. With the container depicted in FIG. 1, the contact areas 7 are disposed at the bottom side of (underneath) electrodes 4, 5 what becomes apparent from view c). In this embodiment, the electrodes 4, 5 are made of a polymer doped with conductive material. The contact areas 7 comprise a contact material that is attached to the conductive polymer very tight, preferably by effect of pressure and heat, i.e. by hot-embossing. The contact material has a lower specific resistance (at 23° C.) and input or boundary resistance, respectively, than the conductive material of which the electrodes 4, 5 are made. In the present embodiment, the contact areas comprise a copper foil that is attached to the electrodes 4, 5 using hot-embossing. As it further becomes apparent from view c), all first electrodes 4 comprise a common contact area 8, i.e. for example, the part of all electrodes of the container 1, which show the same polarity when voltage is applied, e.g. all cathodes if direct current is used. Said contact area 8 comprises a continuous strip or band which extends to all first electrodes 4 and covers them completely. Thus, all first electrodes 4 of said container 1 are conductively coupled. It is an advantage of this measure that the container 1 according to the invention can be easily manufactured at low costs and that the homopolar electrodes can be electrically contacted via a single electric connection resulting in a significant reduction of complexity. The respective second electrode 5 of a chamber 2 comprises a contact area 9 that is specifically allocated to it. Hence, the second electrodes 5 of every chamber 2 can be separately connected via individual contact areas 9. Thus, the generation of electric fields in each chamber 2 can be separately operated. Separately controlling each chamber 2 is advantageous because electrical parameter can be adjusted for each chamber individually so that different conditions can be applied to individual cell suspensions and probes, respectively, which are placed in different chambers 2.

In the present embodiment, 16 chambers 2 are arranged in two rows 10, 11, each row comprising eight chambers 2. Due to this arrangement in rows the first electrodes 4 that are respectively disposed on the same side of one row 10, 11 and the first electrodes 4 of adjoining rows 10, 11, which are respectively oppositely disposed, can be electrically coupled.

Thus, the manufacture of the container 1 according to the invention is simplified, less material is needed and additionally electric contacting is eased. As in this embodiment the contact areas 7, 8, 9 are disposed at the bottom side of, i.e. underneath, the electrodes 4, 5 on the ground 13 of the container 1 electric contacting can be accomplished from the bottom. Thus, constructional effort can be further reduced, in particular if container with many chambers, e.g. 96 or more, shall be used. Additionally, since both electrodes 4, 5 can be contacted from the bottom the use of electrodes that dip into the cell suspension from above can be avoided what has a positive effect on homogeneity of the electric field within the gap 6.

Figure 2:
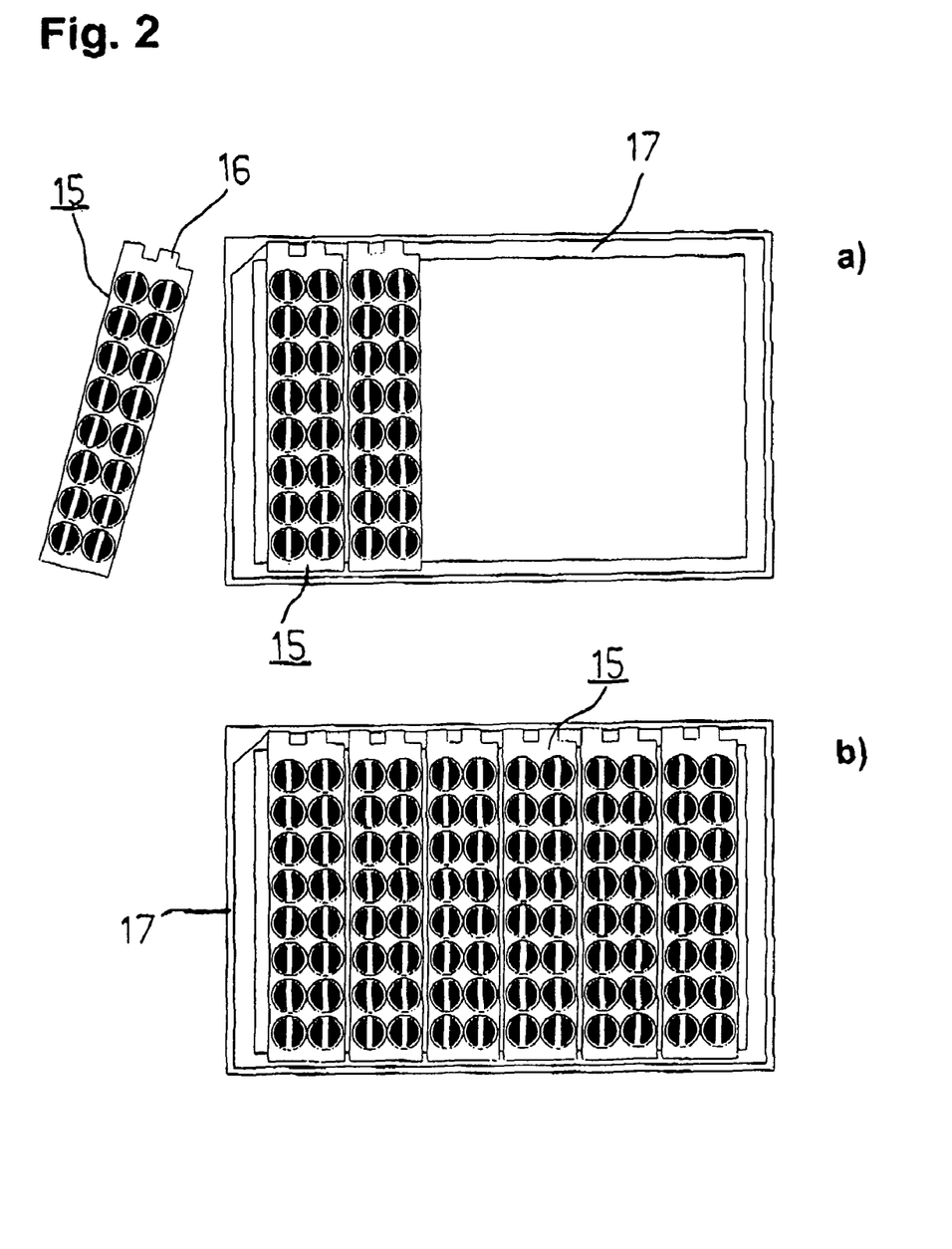
FIG. 2 shows different top views of special embodiments of the devices according to the invention, which are strips that can be inserted into a frame especially designed therefor,
 a) frame partially loaded,
 b) frame entirely loaded.
Figure 3:
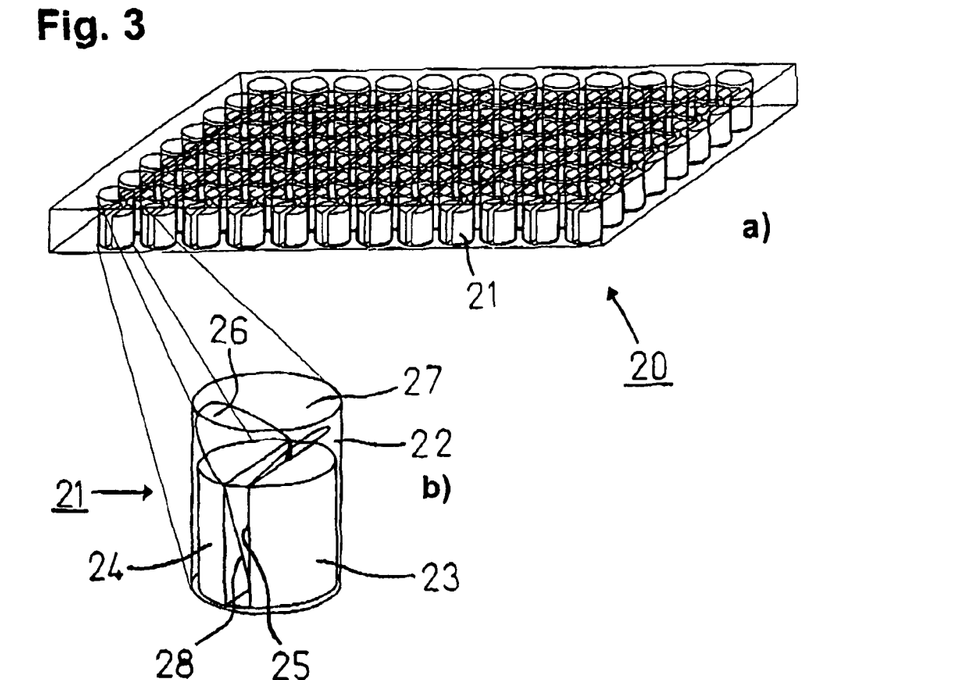
FIG. 3 shows a perspective representation of an embodiment of the container according to the invention, having 96 chambers,
 a) entire microtiter plate,
 b) special representation of a chamber.

FIG. 2 shows a top view of a particular embodiment of containers 15 according to the invention, which generally correspond to the container 1 according to FIG. 1. The Containers 15 are also designed strip-like and comprise a special fastening member 16 at least at one free top end, which serves for fastening the strip in a frame 17. As depicted in view a), single containers 15 which each comprise 16 chambers may be inserted into the frame 16 and removed therefrom. Thus, the frame 17 may be reused even if the individual containers 15 have to be disposed. As a result, less material is needed and environmental compatibility can be improved. Furthermore, the system shown may be variably equipped with different numbers of chambers depending on the size of the frame 17. View b) shows a completely loaded frame 17 that is equipped with six containers 15. Thus, 96 chambers can be used what corresponds to a standard microtiter plate FIG. 3 shows a further embodiment of a container 20 according to the invention, which generally corresponds to the container 1 according to FIG. 1. Contrary to container 1 described above container 20 comprises a total of 96 chambers which are arranged in twelve rows with each row comprising eight chambers 21. One single chamber 21 is schematically depicted in perspective view. This chamber 21 has a wall area 22 made of a conductive polymer, which is formed like a cylinder. The chamber 21 further includes a pair of electrodes that comprises a first electrode 23 and a second electrode 24. Both electrodes 23, 24 define a gap 25 which serves for receiving a suspension of cells and the probe, respectively. The wall area 22 of the chamber 21 is open at the top so as to allow for filling the gap 25, wherein the inner surface 26 narrows to the inside from the opening 27 in direction of the gap 25. Due to this funnel-like design of opening 27 charging of the chamber 21 is facilitated as the opening 27 guides pipette tips. The gap 25 further narrows due to lateral tapering of the sidewall 28 in direction of the bottom so that it actually ends in the ground region like a tip. Thus, it is ensured that also small volume, for example less than 100 µl, can be received by the gap 25 between the electrodes 23, 24. Furthermore, this design of the gap 25 allows for adapting the chamber 21 for receiving various amounts without having to vary the outer dimension of the chamber 21 and hence the entire chamber 21. Consequently, this is especially beneficial if the container 20 is provided for automated processes. In order to adapt the chamber 21 to a different volume merely the inclination of the sidewall 28 has to be varied in the manufacturing process.

Figure 4:
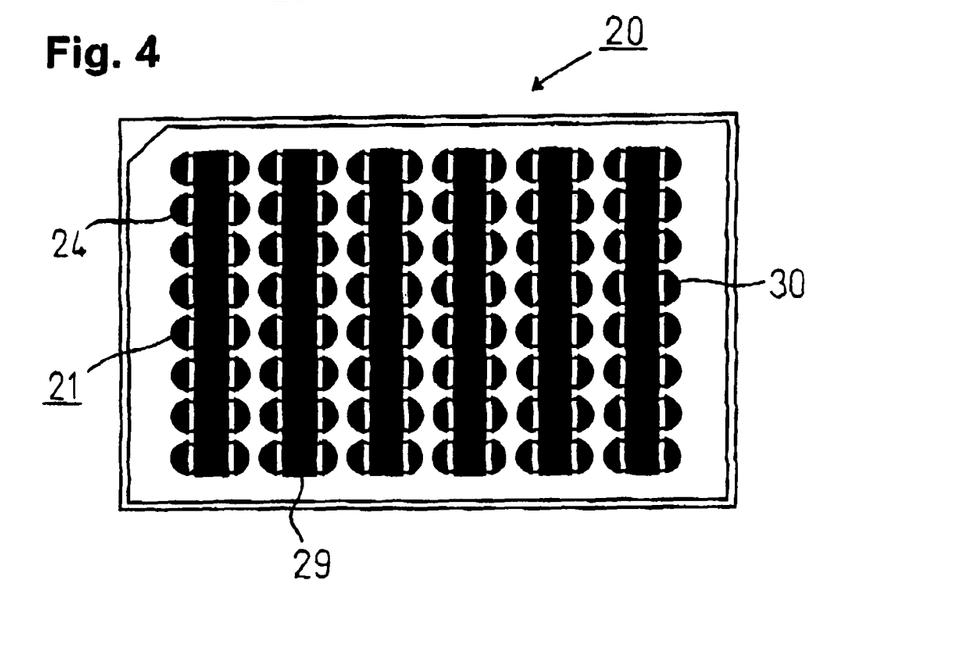
FIG. 4 schematically shows a top view of the bottom side of said device according to FIG. 3.

FIG. 4 shows the bottom side of the container 20 according to FIG. 3. As with the container 1 according to FIG. 1 *c*) also in this embodiment the first electrodes of two adjacent rows, which are not visible in this representation, i.e. for example electrodes that show the same polarity when direct voltage is applied, comprise a common contact area 29. Thus, in this example 16 chambers 21 are always electrically coupled via their first electrodes 23. The container 20 hence comprises a total of six common contact areas 29. The respective second electrodes 24 of each chamber 21, which show opposite polarities, for example, if direct voltage is applied, are not coupled at all, each second electrode 24 comprising its own contact area 30. Due to this specific arrangement the manufacture of the container 20 according to the invention is simplified while separate control of every individual chamber 21 is still possible. Electric coupling of a plurality of first electrodes of a container reduces the overall constructional effort and further allows for effective and safe contacting of the electrodes from the bottom. This will become apparent from FIGS. 5 and 6, respectively.

In the embodiments described above, each electrode 4, 5, 23, 24 is designed like a semi-circle. However, electrodes may at least partially also be formed, for example, like a plate, i.e. flat. In a preferred embodiment, the electrodes are designed, for example, semicircle-like at the bottom of the container and plate-like above along the gap. But there are alternative designs possible as well.

Figure 5:
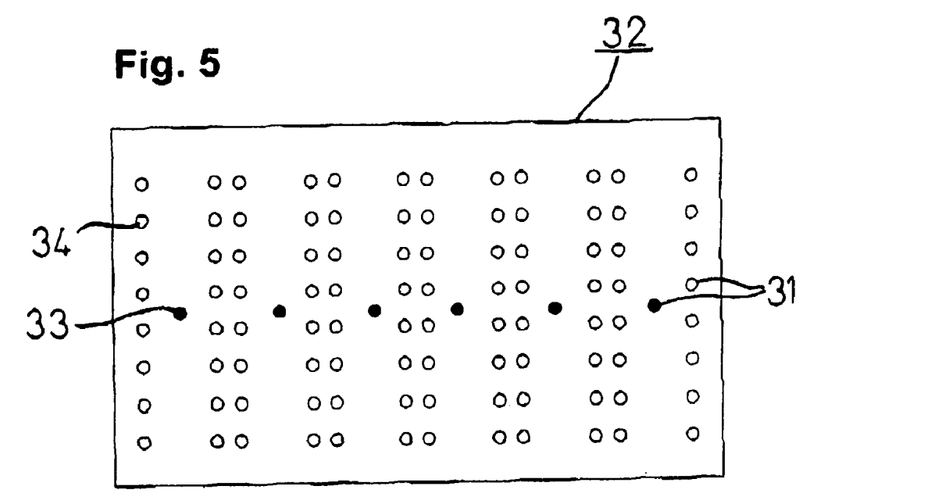
FIG. 5 shows a schematic representation of the arrangement of contact elements of the device according to the invention.

FIG. 5 shows a schematic representation of an arrangement of contact elements 31 in a device according to the invention for contacting of containers according to the invention. The contact elements 31 are arranged on or within a construction 32 that is specifically designed therefor. Said construction 32 may be e.g. a plate or a framework. Said contact elements 31 may be e.g. pin contacts, spring contacts or the like. In the present embodiment, the contact elements 31 are arranged on the construction 32 such that they are particularly suited for electric contacting of the inventive container 20 according to FIGS. 3 and 4, respectively. The various contact elements 33 that are depicted as black dots in this representation are provided for contacting the electrically coupled first electrodes and common contact areas, respectively. In contrast, the contact elements 34 that are depicted in white colour in this representation are provided for contacting the second electrodes which can be contacted separately. Thus, in said embodiment one contact element 34 is respectively provided for each non-coupled second electrode while only one contact element 33 is provided for all electrically coupled first electrodes. Merely one contact element 33 is hence needed for one double-row of chambers. Additionally, all contact elements 33 may be electrically coupled so as to significantly reduce the number of electrical connections. Thus, manufacturing costs and constructional effort can be reduced. However, since individual contact elements 34 are allocated to each chamber separate control of each chamber is maintained.

Figure 6:
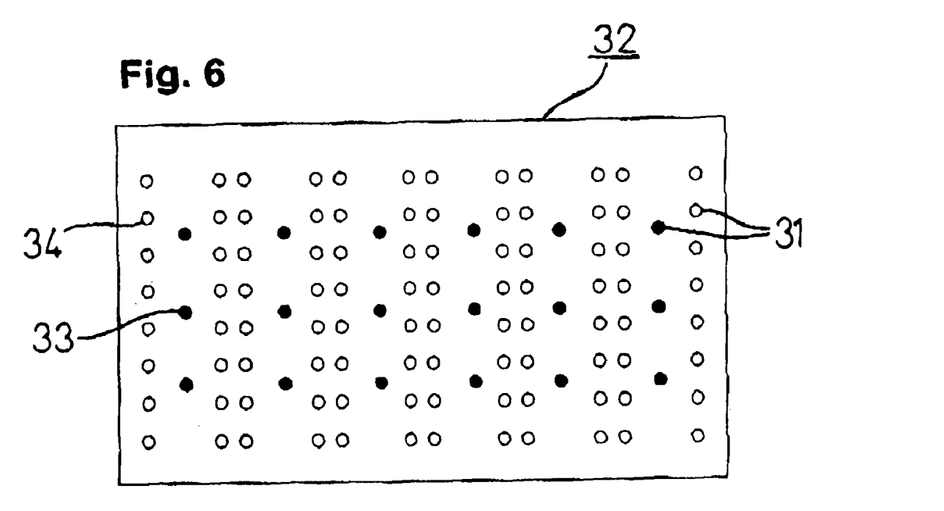
FIG. 6 shows a schematic representation of another embodiment of the arrangement of contact elements in a device according to the invention.

FIG. 6 shows an alternative arrangement of contact elements 31, which corresponds to the one according to FIG. 5, except the feature that a total of three contact elements 33 is provided for the coupled electrodes. These three contact elements 33 are arranged in a row along the common contact area of the coupled second electrodes. By providing two additional contact elements 33 electric contacting can be improved. Furthermore, the likelihood of bad or missing contacting can be significantly decreased. This embodiment also allows for the use of two of these three contact elements 33 for measuring resistance in order to verify the presence of single containers 15 in the frame 17 according to FIG. 2.

The contact elements 31 are arranged on the construction 32 according to FIGS. 5 and 6 such that, for example, the bottom side of the container 20 according to FIGS. 3 and 4 can be simply applied onto the construction 32 in order to achieve electric contacting. The arrangement of the contact elements 31 exactly corresponds to the arrangement of the contact areas 29, 30 of the coupled first electrodes and the non-coupled second electrode 24, respectively.

Figure 7:
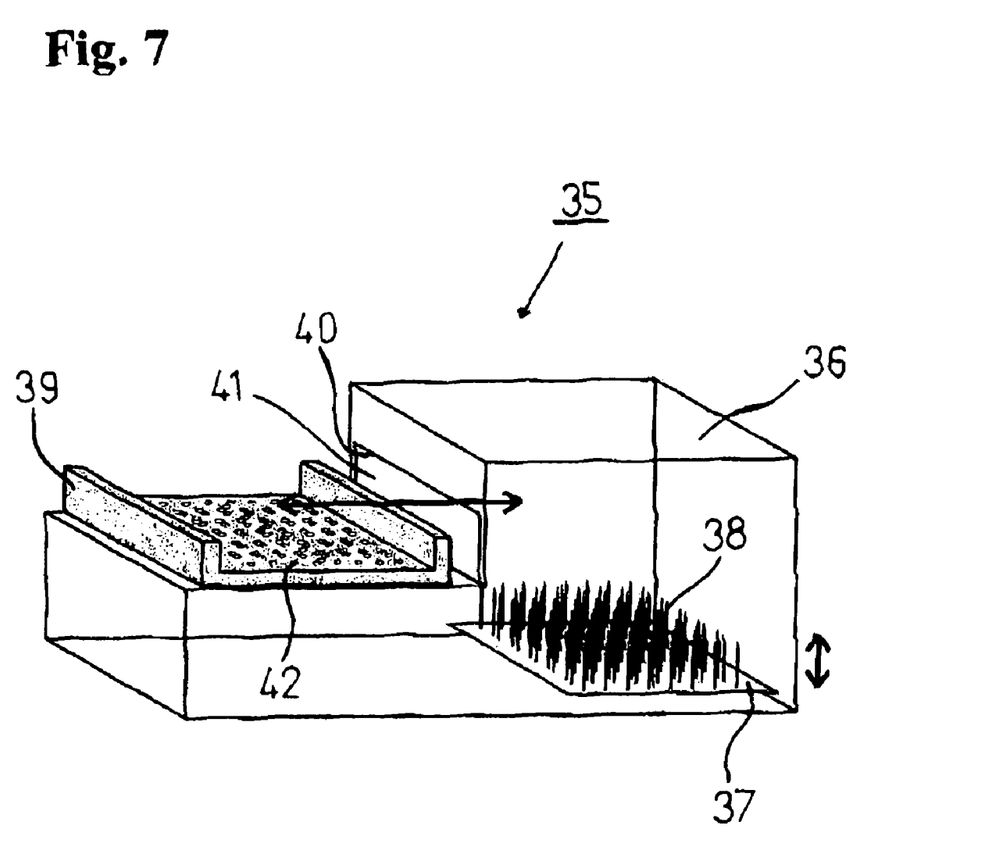
FIG. 7 shows a perspective and schematic representation of a device according to the invention for electrically contacting a container according to the invention.

FIG. 7 shows a perspective and schematic representation of a device 35 according to the invention for contacting containers according to the invention. The device 35 comprises a housing 36 and a plate 37 being disposed within said housing 36, onto which pin-like contact elements 38 are fixed. The plate 37 corresponds to the construction 32 according to FIGS. 5 and 6, respectively. The plate 37 is vertically mobile, wherein the mechanism for moving said plate 37 is not depicted in detail in this representation. The device 35 further comprises a platform 39 that is horizontally mobile, wherein the mechanism for moving said platform 39 is also not depicted in detail in this representation. The platform 39 can be moved into the inner space 41 of the housing 36 through the opening 40 of said housing 36. Hence, the housing 36 is actually a kind of garage within which electric discharge may occur. This is advantageous due to safety reasons as high voltage pulses are used, for example with electroporation, which possibly are hazardous for the user. In this embodiment, the user merely has to place the container including the probes onto the platform 39 without the need of further contacting the device 35 according to the invention during the further proceedings. For example, if a container according to the invention, e.g. the container 20 according to FIGS. 3 and 4, is applied to the platform 39, the platform 39 including the container is subsequently moved through the opening 40 into the inner space 41 of the housing 36 of the device 35 according to the invention. This may be accomplished automatically by means of a motor-driven mechanism. When the platform 39 including the container is completely situated in the inner space 41 the plate 37 including the contact elements 38 is moved upward. Thereby, the pin-like contact elements 38 are inserted through respective holes 42 of the platform 39 so that they can contact the contact areas of the container. Thus, electric contact between the contact elements 38 and the electrodes of the container is established. Subsequently, within the protective housing 36 voltage pulses for generating electric fields in the individual chambers can be activated.

The device 35 according to the invention is also well suited for contacting of containers according to the invention in fully automated processes, in particular for methods which are characterized by very high throughput. A safe and reliable implementation of such methods is ensured by the device according to the invention. In an alternative and different embodiment it would also be possible to leave the platform including the container outside the housing and to move only the construction with the contact elements vertically and/or horizontally in order to contact the electrodes. In this case, electric contact might be accomplished only when the user has already placed the container onto the platform and does not touch the device anymore. As in fully automated processes application of the container is not accomplished by hand but mechanically this alternative embodiment would also be advantageous because a compact construction of the device according to the invention is possible.

Figure 8:
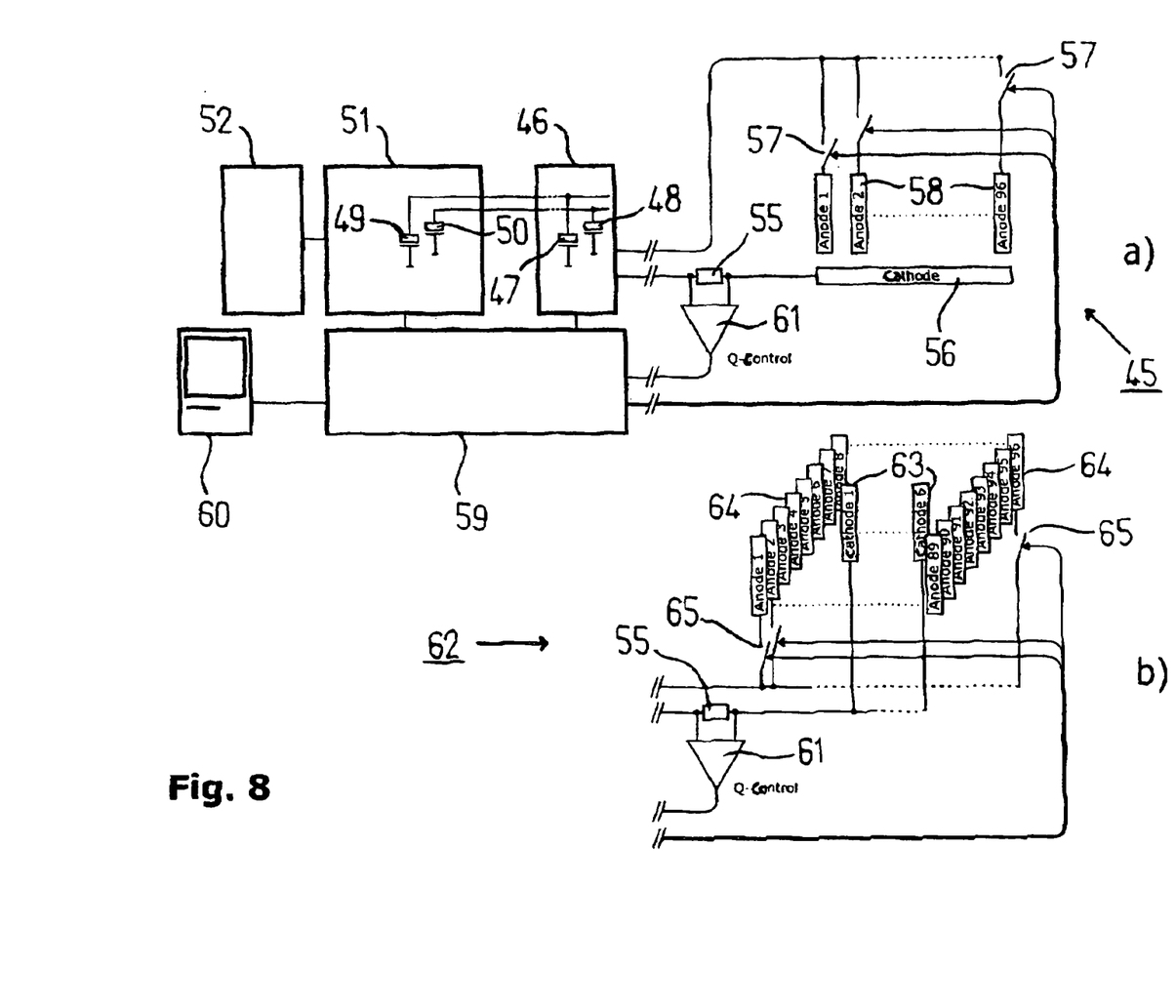
FIG. 8 shows circuit diagrams of an arrangement for the implementation of the method according to the invention,
 a) embodiment with a common/joint cathode,
 b) embodiment for an arrangement of contact elements according to FIG. 5.

FIG. 8 a) shows a schematic circuit diagram of an embodiment of an arrangement 45 according to the invention for the implementation of the method according to the invention. The arrangement 45 comprises a pulse generator 46 which includes two storage units 47, 48. These storage units 47 and 48, respectively, are capacitors that are charged to a predetermined electric charge and which can deliver defined voltage pulses by selective discharge. The storage units 47, 48 are charged to a preset charge by additional storage units 49, 50, which may also be capacitors, of an energy storage unit 51. For this, the storage units 49, 50 are energized by a power supply 52. Interposing additional storage units 49, 50 between the power supply 52 and the storage units 49, 50 is beneficial because the storage units 47, 48 can be charged faster and thus faster series of pulses are possible. The storage units 47, 48 are directly connected to power semiconductors (not shown) by which the selective discharge of the storage units 47, 48 is controlled. The power semiconductors may be, for example, an IGBT or a MOSFET. But other electronic components may also be used, which allow for controlling of voltages or currents to be operated with the necessary circuit time. The use of two storage units 47, 48 allows for delivering two voltage pulses which follow one after the other with short or without interruption. This may be advantageous with the electroporation of specific cell types. In such specific applications, a high voltage pulse of short duration is followed by a longer low voltage pulse, wherein the second pulse may follow the first pulse without interruption.

In the present embodiment, the pulse generator 46, i.e. the storage unit 47 as well as the storage unit 48, is connected to a common electrode 56 via a sensor resistor 55. The common electrode 56 may be, for example, an electrode plate which is disposed in the bottom region of a container according to the invention and extends over all chambers, in this embodiment 96. Thus, in this embodiment all first electrodes of a container are electrically coupled, i.e. show the same polarity when direct voltage is applied. Furthermore, the storage units 47, 48 are connected to the respective second electrodes of the chamber via switch elements 57 that are exclusively allocated to one chamber. The switch elements 57 are preferably relays. The second electrodes 58 which show an opposite polarity in relation to the electrode 56 when e.g. direct voltage is applied are single pin-like electrodes that dip from above into the chamber and the cell suspension or the probe, respectively. Since one relay is allocated to each second electrode 58 of one of the 96 chambers every chamber can be separately switched and controlled, respectively, so that the respective voltage pulse delivered by the pulse generator 46 exclusively leads to the generation of an electric field in the respectively activated chamber. Due to the electrical coupling of the first electrodes resulting in one common electrode 56 the constructional effort, that is in particular the wiring of single electrodes, can be significantly reduced. In this embodiment, the 96 chambers of the container can be separately activated via the 96 switch elements 57 so that the electrical parameter can be varied in every single chamber. Preferably, the switch elements 57 are connected sequentially, i.e. generation of electric fields in different chambers is accomplished successively. Alternatively, e.g. two pulse generators may be provided so as to allow for operating two relays in parallel in order to enhance, for example, the overall operating speed. However, in this case the chambers of the container have to be divided into two regions which each must be connected to a pulse generator so that the overall constructional effort is increased.

Charging the storage units 49, 50 and the storage units 47, 48 as well as operating the power semiconductors and the switch elements 57 is controlled by a control unit 59 that may be operated, for example, by a conventional computer 60. In the present advantageous embodiment, during application of the voltage pulse the electric current may be measured by means of the adjustment unit 61 via the sensor resistor 55 so as to allow for controlling the process by the overall charge delivered which is determined by integration of the current in a preset time slice (Q control). Thereby, the control unit 59 may cause, for example, that the respective relay is opened as soon as a predetermined overall amount of charge is reached. The control of the method according to the invention by the control unit 59 is discussed in detail with reference to FIG. 9.

FIG. 8 b) shows a further embodiment of an arrangement 62 for implementation of the method according to the invention, which generally corresponds to the arrangement 45 according to FIG. 8 a). The arrangement 62 differs from the arrangement 45 as previously described in that there is no common first electrode but a total of six groups of first electrodes 63, which are electrically coupled. This embodiment is well suited for use with the container 20 according to FIGS. 3 and 4 and the construction 32 according to FIG. 5, respectively. The respective first electrodes 63 of two rows of eight respective chambers of one container, i.e. a total of 16 electrodes, are electrically coupled, i.e. have a common contact area. Thus, in this embodiment the pulse generator is connected via the sensor resistor 55 to a total of six contact areas in respect of the coupled first electrodes 63. The respective second electrodes 64 of each chamber are each connected to the pulse generator via switch elements 65. As in this embodiment each second electrode of a chamber can be separately activated via a switch element 65 which is exclusively assigned to the respective second electrode the generation of electric fields in each of the 96 chambers can be separately controlled and the respective chamber to be activated can be freely chosen.

Figure 9:
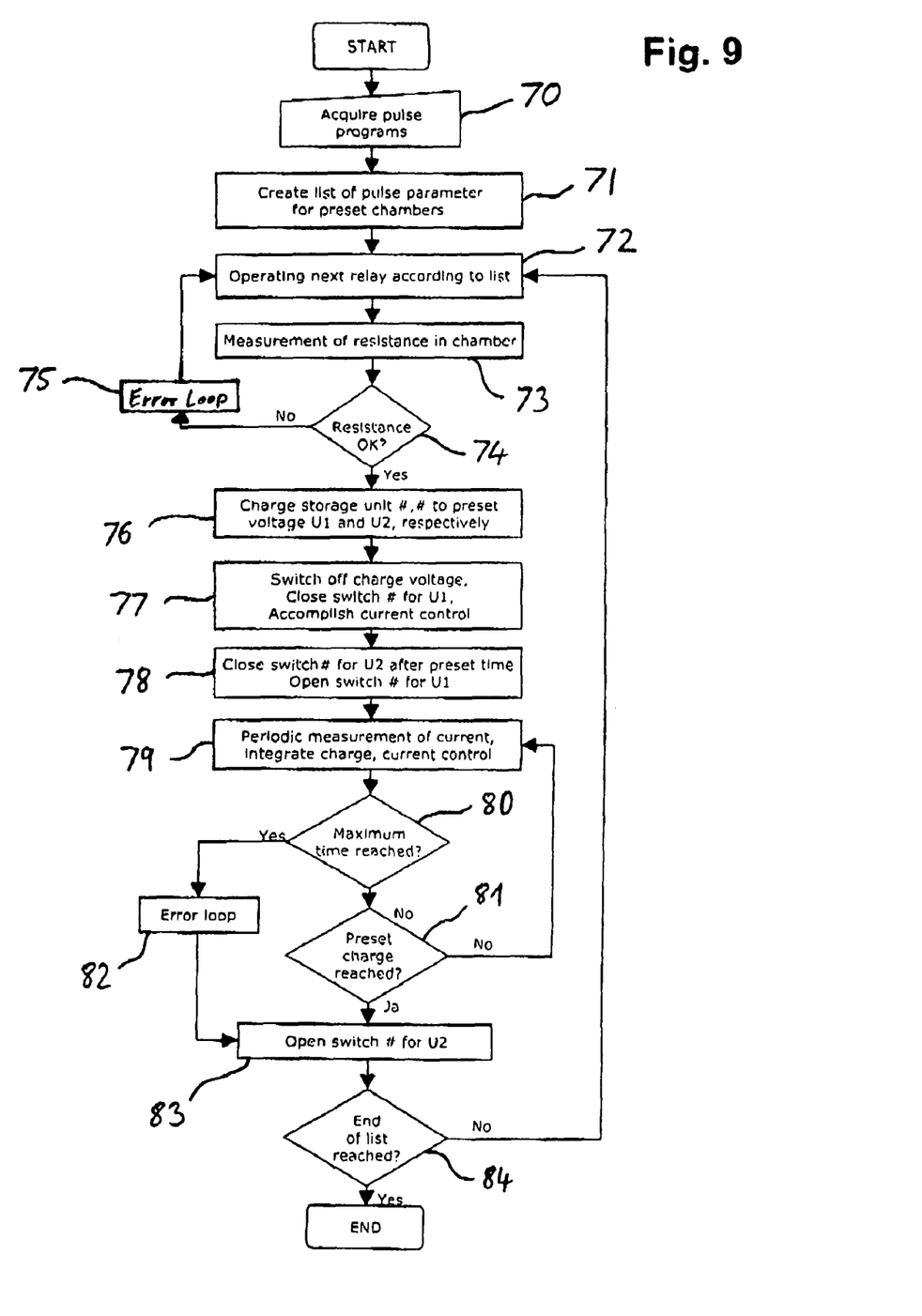
FIG. 9 shows a flow-chart which shows the separate steps of one embodiment of the method according to the invention.

FIG. 9 shows a flow-chart which shows the separate steps 70 to 84 of one embodiment of the method according to the invention. After the start of the routine at first the programs for the voltage pulses are acquired in step 70. Subsequently, in step 71 a list of pulse parameter is created for the preset chambers. In step 72 the first and next switch element, respectively, or depending on the specific embodiment the first and next switch elements, respectively, which allow(s) for separate activation of the preset chamber or chambers, is (are) then operated according to the list of step 71. In step 73 the electric resistance of the chamber to be activated is measured. In step 74 the resistance measured is compared to a target value. If the resistance measured is not in the target range, e.g. if the chamber is empty, in step 75 the routine goes back to step 72 and the next switch element(s) in the list is (are) operated, i.e. the routine switches to the next preset chamber, whereby the error loop is passed through again. If the resistance lies within the target range, i.e. if the chamber is filled with a correct suspension of cells, then the routine switches to step 76. In step 76 the storage unit is or the storage units are charged to the preset voltage (U1) or the preset voltages U1 and U2, respectively. If one storage unit is provided the method according to the invention is realized with one voltage pulse having the voltage U1. If, in contrast, two storage units are provided the method according to the invention can be realized with two voltage pulses which follow each other with short or without interruption, the pulses having the voltage U1 and U2, respectively. In step 77 the voltages for charging the storage units are switched off and the power semiconductor for the first storage unit (U1) is closed so that the preset chamber is exposed to the voltage pulse. Hereby, the current flow can be measured and controlled via a sensor resistor. If one storage unit and one voltage pulse, respectively, is used the routine switches directly to step 79 or step 80. Alternatively, also the power semiconductor of the first storage unit (U1) can be opened after a preset time, wherein the routine directly switches to step 84. In contrast, if two storage units for delivering of two voltage pluses are used the routine firstly switches to step 78. In step 78 the power semiconductor of the first storage unit (U1) is opened after a preset time while the power semiconductor of the second storage unit (U2) is closed in order to deliver the second voltage pulse. In step 79 the charge is integrated using the periodically measured values of electric current so as to determine the respective overall charge. In step 80 at first it is determined whether the preset maximum duration of the voltage pulse(s) is reached. In the positive case, the voltage pulse is interrupted via the error loop (step 82), i.e. the routine switches to step 83. If the maximum duration of the pulse is not reached it is determined in step 81 whether the preset overall charge is reached. In the negative case, the routine steps back to step 79 and the loop is run through again. If the preset overall charge is reached the routine switches to step 83 in which the power semiconductor of the first storage unit (U1) or, if applicable, the second storage unit (U2) is opened. In step 84 it is determined whether the end of the list is reached. In the negative case, the routine steps back to step 72 and the whole loop is run through again. If the end of the list is reached the routine is ended. The generation of electric fields in each chamber is thus controlled separately, wherein the pulse parameter can be preset and controlled separately for any individual chamber. Generation of electric fields in each single chamber is accomplished sequentially, wherein the sequence or order of the chambers to be activated can be preset arbitrarily.

REFERENCE NUMBERS

1 Container
2 Chamber
3 Wall area
4 First electrode
5 Second electrode
6 Gap
7 Contact area
8 Contact area
9 Contact area
10 Row
11 Row
12 Underneath
13 Ground
15 Container
16 Fastening member
17 Frame
20 Container
21 Chamber
22 Wall area
23 First electrode
24 Second electrode
25 Gap
26 Surface
27 Opening
28 Sidewall
29 Contact area
30 Contact area
31 Contact element
32 Construction
33 Contact element
34 Contact element
35 Device
36 Housing
37 Plate
38 Contact element
39 Platform
40 Opening of housing
41 Inner space
42 Holes
45 Arrangement
46 Pulse generator
47 Storage unit
48 Storage unit
49 Storage unit
50 Storage unit
51 Energy storage unit 52 Power supply
55 Sensor resistor
56 Electrode
57 Switch element
58 Electrode
59 Control unit
60 Computer
61 Adjustment unit
62 Arrangement
63 First electrode
64 Second electrode
65 Switch element
70-84 Step

What is claimed is:

1. Container with chambers each of said chambers comprising
at least one pair of electrodes comprising a first and a second electrode for applying an electric voltage to generate an electric field within at least one of said chambers,
wherein
several chambers are disposed in at least two parallel rows,
at least a part of the first electrodes disposed on the same side of the different chambers of one row are conductively coupled,
at least one second electrode of at least one of said chambers is separately conductively connectable, wherein specific contact areas that are electrically contactable for applying said electric voltage are allocated to said second electrodes and
at least two oppositely arranged first electrodes of different chambers of adjacent rows are coupled conductively via a common contact area, and
wherein said contact areas allocated to said at least one second electrode and said common contact area are disposed at the bottom of said electrodes at the ground of the container, the surface of the bottoms of the first electrodes being substantially covered by said common contact area.

2. Container according to claim 1, wherein at least one of the respective second electrode of a chamber has a contact area that is specifically allocated to it.

3. A container according to claim 2, wherein said contact area comprises a contact material which is attached to said electrode and which has a lower specific resistance or boundary resistance at a temperature of 23° C. than a material of which said electrode is made.

4. A container according to claim 2, wherein said contact area is directly attached to said electrode.

5. A container according to claim 1, wherein the electrodes each have a three dimensional structure that provides for gaps between the first and second electrodes, wherein said gaps are capable of use in electroporation.

6. Container according to claim 1, wherein said contact areas are directly attached to said electrodes.

7. Container according to claim 1, wherein the container comprises 6, 8, 12, 16, 24 32, 48, 64, 96, 128, 192, 384, 1536, 3456 or 6144 chambers.

8. Container of claim 1, wherein at least one electrode comprises a polymer that is doped with a conductive material.

9. Container according to claim 8, wherein the conductive material comprises fibres of carbon, graphite, carbon black and/or carbon-nanotubes.

10. Container of claim 8, wherein the polymer is doped with the conductive material in a concentration of 40 to 80% w/w.

11. Container according to claim 1, wherein said contact area comprises a contact material which is attached to said electrode and which has a lower specific resistance or boundary resistance at a temperature of 23° C. than a material of which said electrode is made.

12. Container according to claim 11, wherein said contact material is a metal or an intrinsically conductive synthetic material and/or wherein said contact material has a specific resistance at a temperature of 23° C. below $1\times10^{-5}$ Ohm·cm.

13. Device comprising at least one container according to claim 1, wherein one contact element, respectively, is provided for at least one of said second electrodes, respectively, of one chamber of said container, and one or a few contact elements are provided for said electrically coupled first electrodes.

14. Device according to claim 13, wherein 1 to 6 contact elements are provided.

15. Device according to claim 13, wherein a plate is provided on which said contact element(s) are arranged.

16. Device according to claim 15, wherein the plate is vertically and/or horizontally movable.

17. Device according to claim 13, wherein a platform for the installation of said container is provided, which is horizontally and/or vertically movable.

18. Device according to claim 17, wherein said platform is provided with at least one opening, or wherein said platform is a punched plate.

19. Device according to claim 13, wherein an inner space is provided in which said contact elements are disposed, and/or wherein at least one opening is provided through which said contact elements can be inserted.

20. Device according to claim 13, wherein an opening of a housing is provided through which the container and/or a platform can be inserted into an inner space.

21. Device according to claim 13 comprising at least one storage unit or being connectable to at least one storage unit.

22. Device according to claim 21, wherein at least one switch element is disposed between said storage unit and said electrodes of said container, and/or wherein a switch element is allocated to each inner space and/or each group of coupled electrodes.

* * * * *

UNITED STATES PATENT AND TRADEMARK OFFICE
CERTIFICATE OF CORRECTION

| | | |
|---|---|---|
| PATENT NO. | : 8,101,401 B2 | Page 1 of 1 |
| APPLICATION NO. | : 11/079192 | |
| DATED | : January 24, 2012 | |
| INVENTOR(S) | : Muller-Hartmann et al. | |

It is certified that error appears in the above-identified patent and that said Letters Patent is hereby corrected as shown below:

Please correct Col. 13, Line 53-54, claim 6 as follows:

-- Container according to claim ~~1~~ 2, wherein said contact areas are directly attached to said ~~electrodes~~ electrode. --

Signed and Sealed this
Twenty-ninth Day of January, 2013

David J. Kappos
*Director of the United States Patent and Trademark Office*